United States Patent [19]

Foxton et al.

[11] 4,385,177
[45] May 24, 1983

[54] CEPHALOSPORINS HAVING A CARBAMOYLALKOX-YIMINOARYLACETAMIDO GROUP AT 7-POSITION

[75] Inventors: Michael W. Foxton, Chalfont St. Giles; Gordon I. Gregory, Chalfont St. Peter; David M. Rogers, Ulverston, all of England

[73] Assignee: Glaxo Laboratories, Ltd., London, England

[21] Appl. No.: 124,109

[22] Filed: Feb. 25, 1980

Related U.S. Application Data

[63] Continuation of Ser. No. 36,653, May 7, 1979, abandoned, which is a continuation of Ser. No. 855,079, Nov. 28, 1977, abandoned.

[30] Foreign Application Priority Data

Nov. 30, 1976 [GB] United Kingdom ............ 49962/76

[51] Int. Cl.³ .................. C07D 501/34; C07D 501/56
[52] U.S. Cl. .................................... 544/22; 544/16; 544/24; 544/25; 544/26; 544/27; 544/28; 544/29; 544/30
[58] Field of Search ............... 544/28, 22, 26, 27, 544/16, 24, 25, 29, 30

[56] References Cited

U.S. PATENT DOCUMENTS

| | | | |
|---|---|---|---|
| 3,944,546 | 3/1976 | Breuer et al. | 544/27 |
| 4,064,346 | 12/1977 | Cook et al. | 544/30 |
| 4,074,047 | 2/1978 | Foxton et al. | 544/27 |
| 4,103,084 | 7/1978 | Bradshaw et al. | 544/27 |
| 4,144,393 | 3/1979 | Bradshaw et al. | 544/30 |

FOREIGN PATENT DOCUMENTS 2460537  7/1975  Fed. Rep. of Germany.

*Primary Examiner*—Paul M. Coughlan, Jr.
*Attorney, Agent, or Firm*—Bacon & Thomas

[57] ABSTRACT

Antibiotic compounds of the general formula

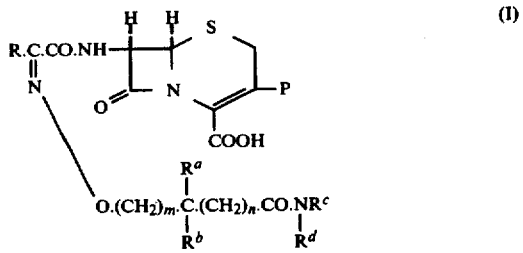

(I)

[wherein R is a phenyl, thienyl or furyl group; $R^a$ and $R^b$, which may be the same or different, are each selected from hydrogen, $C_{1-4}$ alkyl, $C_{2-4}$ alkenyl $C_{3-7}$ cycloalkyl, phenyl, naphthyl, thienyl, furyl, carboxy, $C_{2-5}$ alkoxycarbonyl and cyano, or $R^a$ and $R^b$ together with the carbon atom to which they are attached from a $C_{3-7}$ cycloalkylidene or cycloalkenylidene group; $R^c$ is hydrogen or lower alkyl; $R^d$ is hydroxy, lower alkoxy, aralkoxy or aryloxy; m and n are each 0 or 1 such that the sum of m and n is 0 or 1; and P is selected from a hydrogen atom, a halogen atom and various organic groups] and non-toxic derivatives thereof.

21 Claims, No Drawings

CEPHALOSPORINS HAVING A CARBAMOYLALKOXYIMINOARYLACETAMIDO GROUP AT 7-POSITION

This is a continuation of application Ser. No. 036,653 filed May 7, 1979 which is, in turn, a continuation of Ser. No. 855,079 filed Nov. 28, 1977, both now abandoned.

This invention is concerned with improvements in or relating to cephalosporin compounds, and is more particularly concerned with a novel class of cephalosporin compounds possessing valuable antibiotic properties.

The cephalosporin compounds in this specification are named with reference to "cepham" after *J.Amer.Chem. Soc.,* 1962, 84, 3400, the term "cephem" referring to the basic cepham structure with one double bond.

Cephalosporin antibiotics are widely used in the treatment of diseases caused by pathogenic bacteria in human beings and animals, and are especially useful in the treatment of diseases caused by bacteria which are resistant to other antibiotics such as penicillin compounds, and in the treatment of penicillin-sensitive patients. In many instances it is desirable to employ a cephalosporin antibiotic which exhibits activity against both gram positive and gram negative microorganisms, and a significant amount of research has been directed to the development of various types of broad spectrum cephalosporin antibiotics.

Considerable interest is currently being directed to the development of broad spectrum cephalosporin antibiotics which possess high activity against gram negative organisms. Existing commercially available β-lactam antibiotics tend to exhibit comparatively low activity against certain gram negative organisms, e.g. β-lactamase producing organisms, which are an increasingly common source of infection in humans. The practical therapeutic applications of aminoglycoside antibiotics such as gentamicin which do exhibit activity against gram negative organisms tend to be limited or complicated by the high toxicity of these antibiotics. It is well known that cephalosporin antibiotics normally exhibit low toxicity in man, so that the development of broad spectrum cephalosporin antibiotics possessing high activity against gram negative organisms such as strains of *Escherichia coli* fulfils a significant need in chemotherapy.

The present invention is concerned with 7β-acylamidoceph-3-em-4-carboxylic acid antibiotics and non-toxic derivatives thereof which are characterised in that the said acylamido moiety has the formula

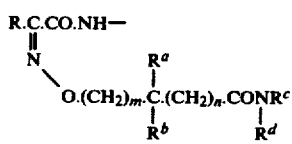

[wherein R is a phenyl, thienyl or furyl group; $R^a$ and $R^b$, which may be the same or different, are each selected from hydrogen $C_{1-4}$ alkyl (e.g. methyl, ethyl, n-propyl, isopropyl or butyl), $C_{2-4}$ alkenyl (e.g. vinyl or allyl), $C_{3-7}$ cycloalkyl (e.g. cyclopropyl, cyclobutyl, cyclopentyl or cyclohexyl), phenyl, naphthyl, thienyl, furyl, carboxy, $C_{2-5}$ alkoxycarbonyl (e.g. ethoxycarbonyl), and cyano, or $R^a$ and $R^b$ together with the carbon atom to which they are attached form a $C_{3-7}$ cycloalkylidene or cycloalkenylidene group (e.g. a cyclobutylidene, cyclopentylidene or cyclohexylidene group); $R^c$ is hydrogen or lower alkyl (e.g. a methyl, ethyl, propyl, isopropyl or t-butyl group); $R^d$ is hydroxy, lower alkoxy (e.g. a methoxy group), aralkoxy (e.g. a mono-, di- or triphenyl-lower alkoxy group such as a diphenylmethoxy or triphenylmethoxy group) or aryloxy (e.g. a phenoxy group); and m and n each 0 or 1 such that the sum of m and n is 0 or 1].

The antibiotic compounds of the present invention may be represented as compounds of the general formula:

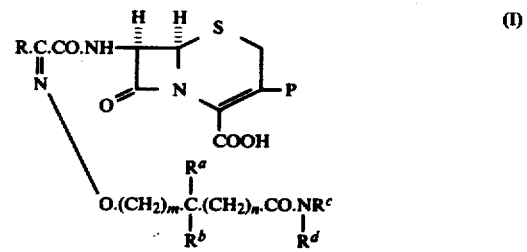

[wherein $R, R^a, R^b, R^c, R^d$, m and n are as hereinbefore defined and P represents a hydrogen atom; a halogen atom such as fluorine, chlorine or bromine; or an organic group, for example a saturated or unsaturated, substituted or unsubstituted, organic group containing 1–20 carbon atoms] and non-toxic derivatives thereof.

These compounds are syn isomers or existing as mixtures of syn and anti isomers containing at least 75% of the syn isomer, preferably at least 90% of the syn isomer.

The antibiotic compounds of formula I may be used to treat a wide variety of diseases caused by pathogenic bacteria in human beings and animals such as respiratory tract and urinary tract infections.

These compounds, especially when $R^c$ is hydrogen and $R^d$ is hydroxy, methoxy, ethoxy or phenoxy exhibit broad spectrum antibiotic activity. The compounds exhibit activity against microorganisms which produce β-lactamases, and also possess very high stability to β-lactamases produced by a range of gram negative organisms.

Compounds according to the invention have been found to exhibit good activity against various members of the Enterobacteriaceae (e.g. strains of *Escherichia coli, Klebsiella aerogenes* and *Proteus mirabilis*).

Compounds wherein at least one of $R^a$ and $R^b$ is other than hydrogen have also shown activity against Pseudomonas organisms e.g. strains of *Pseudomonas aeruginosa*.

The compounds of the invention are defined as having the syn isomeric form as regards the configuration of the group

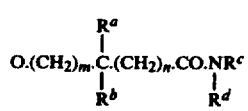

with respect to the carboxamide group. In this specification the syn configuration is denoted structurally as

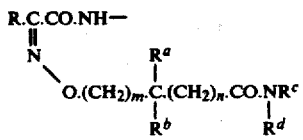

this configuration being assigned on the basis of the work of Ahmad and Spenser reported in Can. J. Chem., 1961, 39, 1340. As indicated above, the compounds may exist as mixtures of syn and anti isomers provided that such mixtures contain at least 75% of the syn isomer, preferably at least 90% of the syn isomer. We prefer, however, the compounds to be syn isomers essentially free from the corresponding anti isomer.

By "non-toxic derivatives" is meant those derivatives which are physiologically acceptable in the dosage at which they are administered. Such derivatives may include, for example, salts, biologically acceptable esters, 1-oxides and solvates (especially hydrates). It will be appreciated that where $R^a$ or $R^b$ is carboxy, derivatives such as salts and esters may be formed by reaction of either or both of the carboxy groups present in such compounds of formula I.

Non-toxic salt derivatives which may be formed from the compounds of general formula I include inorganic base salts such as alkali metal salts (e.g. sodium and potassium salts) and alkaline earth metal salts (e.g. calcium salts); organic base salts (e.g. procaine, phenylethylbenzylamine, dibenzylethylenediamine, ethanolamine, diethanolamine, triethanolamine and N-methylglucosamine salts); and, where appropriate, acid addition salts, e.g. with hydrochloric, hydrobromic, sulphuric, nitric, phosphoric, trifluoroacetic, toluene-p-sulphonic and methane sulphonic acids. The salts may also be in the form of resinates formed with, for example, a polystyrene resin or cross-linked polystyrene divinylbenzene copolymer resin containing amino or quarternary amino groups, or, where appropriate, sulphonic acid groups, or, again where appropriate, with a resin containing carboxyl groups, e.g. a polyacrylic acid resin. Use of highly soluble base salts (e.g. alkali metal salts such as the sodium salt) of compounds of formula I is generally advantageous in therapeutic applications because of the rapid distribution of such salts in the body upon administration. Where, however, insoluble salts of compounds (I) are desired in a particular application, e.g. for use in depot preparations, such salts may be formed in conventional manner, for example with appropriate organic amines.

Biologically acceptable, metabolically labile ester derivatives which may be formed from compounds of formula I include, for example, acyloxymethyl esters, e.g. lower alkanoyloxymethyl esters such as acetoxymethyl, acetoxyethyl or pivaloyloxymethyl esters.

It will be appreciated that when $R^a$ and $R^b$ in the above formulae are different, the carbon atom to which they are attached may comprise a centre of asymmetry; compounds in accordance with the invention wherein $R^a$ and $R^b$ are different may thus be diastereoisomeric. The invention embraces the individual diastereoisomers of such compounds as well as mixtures thereof.

The cephalosporin antibiotics according to the present invention may be unsubstituted at the 3-position or may carry at this position any of the wide range of substituents disclosed in the literature pertaining to cephalosporin compounds, the characterising feature of the invention being the nature of the 7β-acylamido group.

In formula I above P may, for example, be a group of formula $$-XQ$$

wherein X represents oxygen or sulphur and Q represents $C_{1-4}$ alkyl (e.g. methyl or ethyl), $C_{2-4}$ alkenyl (e.g. vinyl or propenyl) or aryl $C_{1-4}$ alkyl (e.g. phenyl $C_{1-4}$ alkyl such as benzyl).

Where P is an unsaturated organic group it may, for example, be a group of the formula

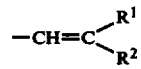

wherein $R^1$ and $R^2$, which may be the same or different, are each selected from hydrogen, carboxy, cyano, $C_{2-7}$ alkoxycarbonyl (e.g. methoxycarbonyl or ethoxycarbonyl), and substituted or unsubstituted aliphatic (e.g. alkyl, preferably $C_1-C_6$ alkyl such as methyl, ethyl, iso-propyl or n-propyl). Specific substituted vinyl groups of the above formula include 2-carboxyvinyl, 2-methoxycarbonylvinyl, 2-ethoxycarbonylvinyl and 2-cyanovinyl.

P may also be an unsubstituted or substituted methyl group, which may be dipicted by the formula $$-CH_2Y$$

where Y is a hydrogen atom or a nucleophilic atom or group, e.g. the residue of a nucleophile or a derivative of a residue of a nucleophile. Y may thus, for example, be derived from the wide range of nucleophilic substances characterised by possessing a nucleophilic nitrogen, carbon, sulphur or oxygen atom described widely in earlier patents and literature pertaining to cephalosporin chemistry. Examples of such nucleophiles includes:

NITROGEN NUCLEOPHILES

Examples of nitrogen nucleophiles include tertiary aliphatic, aromatic, araliphatic and cyclic amines, for example tri($C_{1-6}$ alkyl) amines such as triethylamine, and heterocyclic tertiary amines. The heterocyclic tertiary amines may if desired contain one or more further heteroatoms in addition to the basic nitrogen atom, and may be substituted or unsubstituted. The heterocyclic tertiary amine may thus, for example, be pyridine, pyrimidine, pyridazine, pyrazine, pyrazole, imidazole, triazole or thiazole; a fused bi- or poly-cyclic analogue of any of these heterocycles, for example purine or benzotriazole; and any of the above amines substituted by one or more aliphatic (e.g. $C_{1-4}$ lower alkyl such as methyl), araliphatic (e.g. phenyl lower alkyl such as benzyl), lower alkoxymethyl (e.g. methoxymethyl), acyloxymethyl (e.g. lower alkanoyloxymethyl such as acetoxymethyl), acyl (e.g. formyl or acetyl), acyloxy (e.g. lower alkanoyloxy such as acetoxy), carboxy, esterified carboxy (e.g. lower alkoxycarbonyl such as methoxycarbonyl), carboxy lower alkyl (e.g. carboxymethyl), sulpho, lower alkoxy (e.g. methoxy), aralkoxy (e.g. benzyloxy), alkylthio (e.g. methylthio), cyano, hydroxy, carbamoyl, N-monoloweralkylcarbamoyl (e.g. N-methylcarbamoyl), N,N-diloweralkylcarbamoyl (e.g. N,N-dimethylcarbamoyl), N-(hydroxyloweralkyl)carbamoyl (e.g. N-(hydroxyethyl)carbamoyl), or carbamoylloweralkyl (e.g. carbamoylmethyl) groups. Examples of Y groups which may be obtained from heterocyclic tertiary amine nucleophiles of the above type include pyridinium, 3- and 4-carbamoyl-pyridinium, 3-carboxymethylpyridinium, 3-sulphopyridinium, thiazol -3-yl, pyrazol-1-yl, pyridazinium, and benzotriazol-1-yl.

Another class of nitrogen nucleophiles comprises azides, e.g. alkali metal azides such as sodium azide.

When the group Y is a derivative of a residue of a nitrogen nucleophile it may be, for example, an amino group or an acylamido group. Cmpounds in which Y is amino may be derived from the corresponding compound in which Y is azido by reduction. Compounds in which Y is an acylamido group may be derived by acylation of a compound wherein Y is amino.

Compounds wherein Y is amino may also be reacted with a substituted isocyanate or isothiocyanate to yield urea or thiourea derivatives.

Other compounds in which Y is a derivative of a residue of a nitrogen nucleophile may be obtained by reacting a compound in which Y is azido with a dipolarophile. Examples of suitable dipolarophiles include acetylenic, ethylenic and cyano dipolarophiles.

Acetylenic dipolarophiles may be shown as having the structure

wherein $R^3$ and $R^4$, which may be the same or different, are atoms, e.g. hydrogen atoms, or groups.

In general we prefer that at least one of $R^3$ and $R^4$ should be of an electronegative nature. Examples of such groups include cyano, $CO_2R^5$, $COR^5$ (wherein $R^5$ is, for example, hydrogen, lower alkyl, aryl, lower aralkyl, amino or substituted amino, e.g. monomethyl or dimethylamino), and trihalomethyl e.g. trifluoromethyl.

Where $R^3$ and $R^4$ are discrete atoms or groups which are identical a single compound will result on reaction with the azido cephalosporin; if they are different one will in general obtain a mixture of position isomers.

Ethylenic dipolarophiles may be shown as having the structure

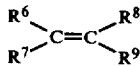

where $R^6$, $R^7$, $R^8$ and $R^9$ which may be the same or different are atoms or groups. One or more of the groups $R^6$ to $R^9$ will preferably be of an electronegative nature. Such groups include, for example, cyano and groups of formula $CO_2R^5$ and $—COR^5$ (wherein $R^5$ is as defined above). $R^6$ and $R^8$ may together form a cyclic structure, e.g. a carbocyclic structure. Examples of carbocyclic ethylenic dipolarophiles include norbornenes and benzoquinone. Examples of non-cyclic ethylenic dipolarophiles include dicyanoethylene and lower mono- and di-alkoxycarbonyl ethylenes.

One or more of $R^6$, $R^7$, $R^8$ and $R^9$ may if desired be electropositive.

Cyano compounds, especially those which are activated by electronegative groups, may function as cyano dipolarophiles. Examples of such dipolarophiles include lower alkoxycarbonyl cyanides and cyanogen.

CARBON NUCLEOPHILES

Examples of carbon nucleophiles include inorganic cyanides, pyrroles and substituted pyrroles, e.g. indoles, and compounds giving stabilised carbanions, for example acetylenes and compounds having β-diketone groups, for example acetoacetic and malonic esters and cyclohexane-1,3-diones or enamines, ynamines or enols.

The carbon nucleophile may thus give rise to cephalosporin compounds characterized by possessing a substituent at the 3-position in which a carbonyl group is linked to the cephalosporin nucleus through two carbon atoms. Such compounds may thus possess as the 3-substituent a group of the formula

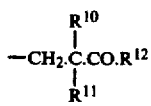

wherein $R^{10}$ and $R^{11}$, which may be the same or different, are selected from hydrogen; cyano; lower alkyl e.g. methyl or ethyl; phenyl; phenyl substituted by, for example, halo, lower alkyl, lower alkoxy, nitro, amino or lower alkylamino; carboxy; lower alkoxycarbonyl; mono- or di-aryl lower alkoxycarbonyl; lower alkylcarbonyl; aryl lower alkyl or $C_5$ or $C_6$ cycloalkyl and $R^{12}$ is selected from hydrogen; lower alkyl e.g. methyl or ethyl; phenyl; substituted phenyl; aryl lower alkyl; lower alkoxy e.g. methoxy or ethoxy; or lower aralkoxy, e.g. benzyloxy and 4-nitrobenzyloxy.

SULPHUR NUCLEOPHILES

Examples of sulphur nucleophiles include thioureas, including aliphatic, aromatic, araliphatic, alicyclic and heterocyclic substituted thioureas; dithiocarbamates; aromatic, aliphatic and cyclic thioamides, for example thioacetamide and thiosemicarbazide; thiosulphates; thiols; thiophenols; thioacids, e.g. thiobenzoic acid or thiopicolinic acid; and dithioacids.

One class of sulphur nucleophile includes those compounds of the formula: $R^{13}.S(O)_nH$ in which $R^{13}$ is an aliphatic e.g. lower alkyl such as methyl, ethyl or n-propyl group; an alicyclic e.g. lower cycloalkyl such as cyclohexyl or cyclopentyl group; an aromatic e.g. $C_{6-12}$ mono- or bicyclic carbocyclic aryl such as phenyl or naphthyl group; an araliphatic e.g. phenyl lower (e.g. $C_{1-4}$) alkyl such as benzyl group; or a heterocyclic group, and n is 0, 1 or 2. A preferred class of nucleophiles falling within the above formula is that having the general formula $R^{14}SH$ in which $R^{14}$ is aliphatic e.g. lower alkyl such as methyl, ethyl or n-propyl or lower alkanoyl such as acetyl; araliphatic, e.g. phenyl lower alkyl such as benzyl or phenethyl or substituted phenyl lower alkyl; alicyclic, e.g. cycloalkyl such as cyclopentyl or cyclohexyl; aromatic, e.g. phenyl, substituted phenyl or a heterocyclic group containing at least one 5- or 6-membered ring and having one or more heteroatoms selected from 0, N and S. Such heterocyclic groups $R^{14}$ may be substituted, and examples of suitable heterocyclic groups include thiadiazolyl, e.g. 5-methyl-1,3,4-thiadiazol-2-yl; diazolyl; triazolyl, e.g. triazol-4-yl; tetrazolyl, e.g. 1-methyltetrazol-5-yl, 1-ethyltetrazol-5-yl, 1-phenyltetrazol-5-yl; or 1-carboxymethyltetrazol-5-yl; thiazolyl; thiatriazolyl; oxazolyl; oxadiazolyl, e.g. 2-phenyl-1,3,4-oxadiazol-5-yl; pyridyl, e.g. N-methylpyrid-2-yl; pyrimidyl; fused heterocyclic ring systems such as benzimidazolyl, benzoxazolyl, benzothiazolyl such as benzothiazol-2-yl triazolopyridyl or purinyl; and substituted versions of such fused ring systems, e.g. nitrobenzothiazol-2-yl such as 5- or 6-nitrobenzothiazol-2-yl.

OXYGEN NUCLEOPHILES

Examples of oxygen nucleophiles include water; alcohols, for example alkanols such as methanol, ethanol, propanol and butanol; and lower alkanoic and alkenoic acids.

The term "oxygen nucleophile" thus includes compounds of the following formula:

$$R^{15}OH$$

in which the group $R^{15}$ may be lower alkyl (e.g. methyl, ethyl, n-propyl, isopropyl, n-butyl or isobutyl); lower alkenyl (e.g. allyl); lower alkynyl (e.g. propynyl); lower cycloalkyl (e.g. cyclopropyl, cyclopentyl or cyclohexyl); lower cycloalkyl lower alkyl (e.g. cyclopropylmethyl, cyclopentylmethyl or cyclohexylethyl); aryl (e.g. phenyl or naphthyl); aryl lower alkyl (e.g. benzyl); heterocyclic (e.g. a heterocyclic group as defined for $R^{14}$, such as N-methylpyrid-2-yl); heterocyclic lower alkyl (e.g. furfuryl); or any of these groups substituted by, for example, one or more of lower alkoxy (e.g. methoxy or ethoxy), lower alkylthio (e.g. methylthio or ethylthio), halogen (chlorine, bromine, iodine or fluorine), lower alkyl (e.g. methyl or ethyl), nitro, hydroxy, acyloxy, carboxy, carbalkoxy, lower alkylcarbonyl, lower alkylsulphonyl, lower alkoxysulphonyl, amino, lower alkylamino or acylamino groups.

In the case in which water is the nucleophile there will be obtained 3-hydroxymethyl cephalosporin compounds. Such 3-hydroxymethyl compounds and nontoxic derivatives thereof may show antibacterial activity and it is of note that they may be metabolites of compounds of general formula I where P is acetoxymethyl. 3-Hydroxymethyl cephalosporins may be acylated to form derivatives characterized by possessing the group 3-$CH_2.O.CO.R^{16}$ or 3-$CH_2.O.CO.AR^{17}$ where A is O, S or NH, $R^{16}$ is an organic group and $R^{17}$ is hydrogen or an organic group.

The group $R^{16}CO-$ or $R^{17}A.CO-$ may be chosen from among the wide class of such groups described in the literature and may have up to 20 carbon atoms. $R^{16}$ and, where appropriate, $R^{17}$ may thus each be a hydrocarbon group or such a group carrying one or more substituent atoms or groups, and may thus be chosen from the following list, which is not intended to be exhaustive:

(i) $C_nH_{2n+1}$ where n is an integer from 1 to 7, e.g. 1 to 4. The group may be straight or branched and, if desired, may be interrupted by an oxygen or sulphur atom or an imino group or substituted by cyano, carboxy, lower alkoxycarbonyl, hydroxy, carboxycarbonyl (HOOC.CO), halogen (e.g. chlorine, bromine or iodine) or amino. Examples of such groups include methyl, ethyl, propyl, isopropyl, n-butyl, t-butyl, sec.-butyl and 2-chloroethyl.

(ii) $C_nH_{2n-1}$ where n is an integer from 2 to 7. The group may be straight or branched and, if desired, may be interrupted by an oxygen or sulphur atom or an imino group. Examples of such groups include vinyl and propenyl.

(iii) $R^{18}$, where $R^{18}$ is carbocyclic aryl (e.g. $C_{6-12}$ mono- or bicyclic carbocyclic aryl), heterocyclic aryl (e.g. comprising a 5- or 6-membered ring containing at least one of O, N and S), lower cycloalkyl, substituted aryl and substituted cycloalkyl. Examples of this group include phenyl; substituted phenyl e.g. hydroxyphenyl, chlorophenyl, fluorophenyl, tolyl, nitrophenyl, aminophenyl, methoxyphenyl or methylthiophenyl; thien-2 and -3-yl; pyridyl; cyclohexyl; cyclopentyl; cyclopropyl; sydnone; naphthyl; and substituted naphthyl e.g. 2-ethoxynaphthyl.

(iv) $R^{18}(CH_2)_m$ where $R^{18}$ has the meaning defined above under (iii) and m is an integer from 1 to 4. Examples of this group include methyl, ethyl or butyl substituted by the various specific $R^{18}$ groups listed under (iii), e.g. lower cycloalkyl $C_{1-4}$ alkyl and carbocyclic or heterocyclic aryl $C_{1-4}$ alkyl such as benzyl and the appropriate substituted benzyl groups.

3-Position substituents of the above type thus include lower alkanoyloxymethyl groups such as acetoxymethyl and isobutyryloxymethyl, lower alkenoyloxymethyl groups such as crotonyloxymethyl; aroyloxymethyl groups such as benzoyloxymethyl; carbamoyloxymethyl, N-(lower alkyl)carbamoyloxymethyl such as N-methylcarbamoyloxymethyl, and N-(haloalkyl)carbamoyloxymethyl such as N-(2-chloroethyl)carbamoyloxymethyl.

A further important class of cephalosporin compounds are those possessing the group 3—$CH_2Hal$ wherein Hal is chlorine, bromine or iodine. Such compounds may be primarily of value as intermediates of use in the preparation of active cephalosporin compounds by replacement of the halogen atom by a nucleophile e.g. a nitrogen-, oxygen- or sulphur-containing nucleophile as hereinbefore described.

The term "lower" as used in this specification and the accompanying claims to qualify aliphatic groups denotes, unless otherwise stated, that the said group may contain up to 6 carbon atoms. "Lower" as used to qualify cycloaliphatic groups indicated that the group may contain 3-7 (e.g. 5-7) carbon atoms.

One class of cephalosporin antibiotics in accordance with the invention comprises compounds of general formula

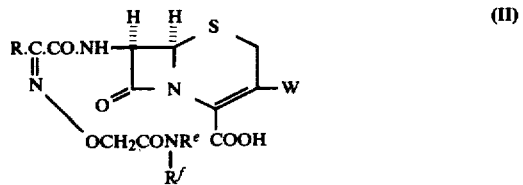
(II)

[wherein R is as hereinbefore defined; $R^e$ represents a hydrogen atom or a methyl group; $R^f$ represents a hydroxy, methoxy, ethoxy, phenoxy, diphenylmethoxy or triphenylmethoxy group; and W is selected from:

(i) acetoxymethyl, (ii) carbamoyloxymethyl, (iii) N-methylcarbamoyloxymethyl, (iv) the group —$GH_2G$ where G is the residue of a nitrogen nucleophile selected from compounds of the formula

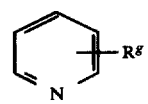

(wherein $R^g$ is hydrogen, carbamoyl, carboxymethyl or sulpho) and pyridazine, and (v) the group —$CH_2SR^w$ wherein $R^w$ is selected from pyridyl, diazolyl, triazolyl, tetrazolyl, thiazolyl, thiadiazolyl, oxadiazolyl, and substituted (e.g. lower alkyl- or phenyl-substituted) versions of these groups such as 1-methyltetrazol-5-yl, 1-phenyltetrazol-5-yl; 1-carboxymethyltetrazol-5-yl, 5-methyl-1,3,4-thiadiazol-2-yl and 5-phenyl-1,3,4-oxadiazol-2-yl] and non-toxic derivatives thereof.

These compounds exhibit broad spectrum antibiotic activity coupled with high β-lactamase stability. A characteristic feature of the compounds is their high activity against strains of *Escherichia coli*, *Klebsiella aerogenes* and *Proteus mirabilis*.

A further class of cephalosporin antibiotics in accordance with the invention comprises compounds of the general formula

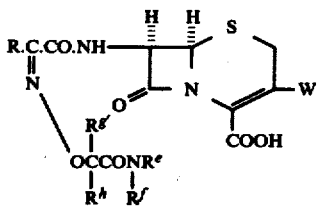

(wherein R, W, $R^e$ and $R^f$ are as hereinbefore defined, and $R^{g'}$ represents methyl, ethyl, propyl, allyl or phenyl and $R^h$ represents hydrogen, carboxy or more preferably, a group as defined for $R^g$; or $R^{g'}$ and $R^h$ together with the carbon atom to which they are attached form a cyclobutylidene, cyclopentylidene or cyclohexylidene group) and non-toxic derivatives thereof.

These compounds exhibit broad spectrum antibiotic activity coupled with β-lactamase stability. A characteristic feature of the compounds is their activity against Pseudomonas organisms such as strains of *Pseudomonas aeruginosa*.

The compounds according to the invention may be prepared by any convenient method, for example by techniques analogous to those described in British Pat. No. 1,399,086.

Thus according to one embodiment of the invention we provide a process for the preparation of an antibiotic compound of general formula I as hereinbefore defined or a non-toxic derivative thereof which comprises either (A) condensing a compound of the formula

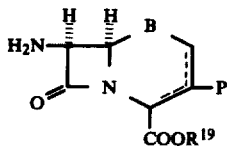

[wherein P is as defined above; B is $>S$ or $>S\rightarrow O$ (α- or β-); $R^{19}$ represents hydrogen or a carboxyl blocking group, e.g. the residue of an ester-forming aliphatic or araliphatic alcohol or an ester-forming phenol, silanol or stannanol (the said alcohol, phenol, silanol or stannanol preferably containing 1–20 carbon atoms) or a symmetrical or mixed anhydride group derived from an appropriate acid; and the dotted line bridging the 2-, 3- and 4-positions indicates that the compound is a ceph-2-em or ceph-3-em compound] or a salt, e.g. an acid addition salt such as a hydrochloride, hydrobromide, sulphate, nitrate, phosphate, methane sulphonate or tosylate, or an N-silylated derivative thereof with an acid of formula

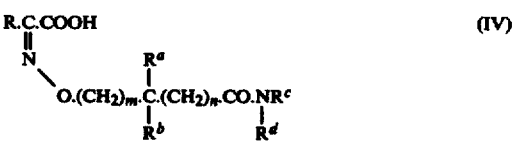

(wherein R, $R^a$, $R^b$, $R^c$, m and n are as hereinbefore defined and $R^d$ is lower alkoxy, aralkoxy or aryloxy) or with an acylating agent corresponding thereto; or (B), where P in formula I is the group —$CH_2Y$ (where Y represents a nucleophilic atom or group) reacting a compound of the formula

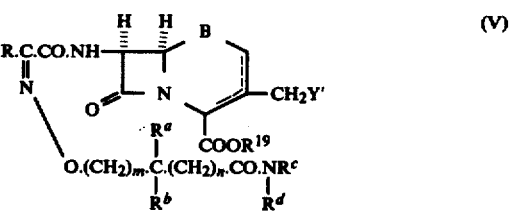

(wherein B, R, $R^a$, $R^b$, $R^c$, $R^d$, $R^{19}$, the dotted line, m and n are as hereinbefore defined; and Y' is a replaceable residue of a nucleophile, e.g. an acetoxy, dichloroacetoxy or hydroxy group or a halogen atom such as chlorine, bromine or iodine) with a nucleophile; whereafter, if necessary and/or desired in each instance, any of the following reactions (C) in any appropriate sequence, are carried out:

(i) conversion of the resulting product (wherein $R^d$ is a readily cleavable lower alkoxy, aralkoxy or aryloxy group) into a compound wherein $R^d$ is hydroxy,
(ii) conversion of a $\Delta^2$ isomer into the desired $\Delta^3$ isomer,
(iii) reduction of a compound wherein B is $>S\rightarrow O$ to form a compound wherein B is $>S$,
(iv) reduction of a 3-azidomethyl compound to form a 3-aminomethyl compound,
(v) acylation of a 3-aminomethyl compound to form a 3-acylaminomethyl compound,
(vi) reaction of a 3-azidomethyl compound with a dipolarophile to form a compound having a polyazole ring linked to the 3-position carbon atom through a methylene group,
(vii) deacylation of a 3-acyloxymethyl compound to form a 3-hydroxymethyl compound,
(viii) acylation of a 3-hydroxymethyl compound to form a 3-acyloxymethyl compound,
(ix) carbamoylation of a 3-hydroxymethyl compound to form an unsubstituted or substituted 3-carbamoyloxymethyl compound,
(x) conversion of a precursor for the desired 7-acylamido group into the desired group, and
(xi) removal of carboxyl blocking groups;
and finally (D) recovering the desired compound of formula I or a non-toxic derivative thereof, if necessary after separation of isomers.

Non-toxic derivatives of the compounds of formula I may be formed in any convenient way, for example according to methods well known in the art. Thus, for example, base salts may be formed by reaction of the cephalosporin acid with sodium 2-ethylhexanoate or potassium 2-ethylhexanoate. Biologically acceptable ester derivatives may be formed using conventional esterifying agents. 1-Oxides may be formed by treatment of the corresponding cephalosporin sulphide with an appropriate oxidising agent, for example with a peracid such as metaperiodic acid, peracetic acid, monoperphthalic acid or m-chloroperbenzoic acid, or with t-butyl hypochlorite, this last reagent conveniently being employed in the presence of a weak base such as pyridine.

Acylating agents which may be employed in the preparation of compounds of formula I include acid halides, particularly acid chlorides or bromides. Such acylating agents may be prepared by reacting an acid (IV) or a salt thereof with a halogenating agent e.g. phosphorus pentachloride, thionyl chloride or oxalyl chloride. Treatment of the sodium, potassium or triethylammonium salt of the acid (IV) with oxalyl chloride is advantageous in that under these conditions isomerisation is minimal.

Acylations employing acid halides may be effected in aqueous and non-aqueous reaction media, conveniently at temperatures of from −50° to +50° C., preferably −20° to +30° C., if desired in the presence of an acid binding agent. Suitable reaction media include aqueous ketones such as aqueous acetone, esters such as ethyl acetate, halogenated hydrocarbons such as methylene chloride, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acids of formula (IV) may themselves be used as acylating agents in the preparation of compounds of formula I. Acylations employing acids (IV) are desirably conducted in the presence of a condensing agent, for examle a carbodiimide such as N,N'-dicyclohexylcarbodiimide. Acylation reactions of this type are desirably effected in an anhydrous reaction medium, e.g. methylene chloride, dimethylformamide or acetonitrile.

Acylation may also be effected with other amide-forming derivatives of acids of formula (IV) such as, for example, a symmetrical anhydride or a mixed anhydride (e.g. with pivalic acid or formed with a haloformate such as a lower alkylhaloformate). The mixed or symmetrical anhydride may be generated in situ; thus, for example, a mixed anhydride may be generated using N-ethoxycarbonyl-2-ethoxy-1,2-dihydroquinoline.

It will be appreciated that in processes for the preparation of compounds of formula I wherein $R^a$ or $R^b$ represents carboxy it will in many instances be necessary to protect the carboxy group; for example by substitution with a carboxyl blocking group, e.g. a group as hereinbefore defined in connection with $R^{19}$.

Any transformations of substituents at the 3-position which may be necessary in the preparation of particular compounds of formula I may, for example, be effected by methods described in the literature.

Thus, for example, compounds substituted at the 3-position by a group

—CH$_2$Y wherein Y represents an ether or thioether group or a halogen atom may be prepared as described in British Pat. Nos. 1,241,656; 1,241,657; 1,277,415 and 1,279,402. Compounds wherein Y is the residue of a nucleophile may also be prepared by the reaction of a 3-acetoxymethyl cephalosporin compound with a nucleophile, for example, pyridine or other tertiary amine as described in British Pat. No. 912,541; a sulphur-linking, nitrogen-linking or inorganic nucleophile as described in British Pat. No. 1,012,943; a sulphur-linking nucleophile as described in British Pat. Nos. 1,059,562; 1,101,423 and 1,206,305; or a nitrogen-linking nucleophile as described in British Pat. Nos. 1,030,630; 1,082,943 and 1,082,962. Compounds in which Y is a derivative of a residue of a nucleophile, e.g. where Y is an amino or acylamido group derived from an azido group may be prepared as described in British Pat. Nos. 1,057,883 and 1,211,694, these patents further describing the reaction of compounds in which Y is azido with a dipolarophile. Compounds wherein Y is the residue of a nucleophile may also be prepared by the reaction of a 3-halomethylcephalosporin with any of the nucleophiles disclosed in the above references, such a process being described in British Pat. No. 1,241,657, or by the reaction of a 3-halomethylcephalosporin sulphoxide with any of the nucleophiles disclosed in the above references, such a process being described in British Pat. No. 1,326,531. The contents of the above mentioned British Patents are herein incorporated for reference purposes.

Compounds possessing a 3-substituent

—CH$_2$Y wherein Y is a hydroxy group may be prepared by the methods described in British Pat. Nos. 1,121,308, 1,399,086 and 1,474,519.

Where Y is a halogen (i.e. chlorine, bromine or iodine) atom, ceph-3-em starting compounds may be prepared by halogenation of a 7β-acylamido-3-methyl-ceph-3-em-4-carboxylic acid ester 1β-oxide followed by reduction of the 1β-oxide group later in the sequence as described in British Pat. No. 1,326,531. The corresponding ceph-2-em compounds may be prepared by the method of Dutch published Patent Application No. 6,902,013 by reaction of a 3-methylceph-2-em compound with N-bromosuccinimide to yield the corresponding 3-bromomethylceph-2-em compound.

Carbamoylation of 3-hydroxymethyl compounds may be effected by conventional methods. Thus, for example, a 3-hydroxymethyl cephalosporin may be reacted with an isocyanate of formula R$^i$.NCO (wherein R$^i$ represents a labile substituent group or an alkyl group) to give a compound containing a 3-position substituent having the formula —CH$_2$O.CONHR$^i$ (wherein R$^i$ has the above defined meaning). Where R$^i$ is a labile substituent this substituent may if desired subsequently be cleaved, e.g. by hydrolysis, to form a 3-carbamoyloxymethyl group. Labile groups R$^i$ which are readily cleavable upon subsequent treatment include chlorosulphonyl and bromosulphonyl; halogenated lower alkanoyl groups such as dichloroacetyl and trichloroacetyl; and halogenated lower alkoxycarbonyl groups such as 2,2,2-trichloroethoxycarbonyl. These labile R$^i$ groups may generally be cleaved by acid or base catalysed hydrolysis (e.g. by base catalyzed hydrolysis using sodium bicarbonate).

Compounds having a vinyl or substituted vinyl group at the 3-position may be obtained by the method described in Belgian Pat. No. 761,897.

The product obtained in accordance with process (A) may, if desired, be converted into a corresponding compound of formula I wherein $R^d$ is hydroxy, for example, by acid-, base- or enzymically- catalysed hydrolysis. For this conversion compounds of formula I wherein $R^d$ is diphenylmethoxy, benzyloxy, t-butoxy or p-nitrobenzyloxy, are particularly preferred.

A ceph-2-em reaction product may be oxidised to yield the corresponding ceph-3-em 1-oxide, for example by reaction with a peracid as mentioned previously; the resulting sulphoxide may, if desired, subsequently be reduced as described hereinafter to yield the corresponding ceph-3-em sulphide.

Where a compound is obtained in which B is $>S\rightarrow O$ this may be converted to the corresponding sulphide by, for example, reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of $-20°$ to $+50°$ C.

Where a compound of formula I is obtained as a mixture of isomers, the syn isomer may be obtained by, for example, conventional methods such as crystallisation or chromatography.

Starting materials of formula III wherein P is hydrogen may, for example, be prepared by the methods of Belgian Pat. No. 774,480 and French Pat. No. 2,165,834. Starting materials of formula III wherein P is a halogen atom (such as fluorine, chlorine or bromine) may, for example, be prepared as described in German OLS No. 2,408,686.

Acids of formula (IV) and acid halides and anhydrides corresponding thereto are novel.

For use as starting materials for the preparation of compounds of general formula I according to the invention, compounds of general formula (IV) and acid halides and anhydrides corresponding thereto in their syn isomeric form or in the form of mixtures of the syn isomers and the corresponding anti isomers containing at least 90% of the syn isomer are preferably used.

Acids (IV) may be prepared by etherification of an acid of formula

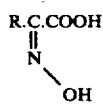  (VI)

(where R has the above-defined meaning) by reaction with a compound of general formula

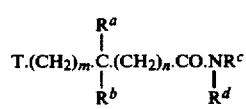  (VII)

(wherein $R^a$, $R^b$, $R^c$, m and n are as hereinbefore defined, $R^d$ is lower alkoxy, aralkoxy or aryloxy and T is halogen such as chloro, bromo or iodo; sulphate; or sulphonate such as tosylate). Separation of isomers may be effected either before or after such etherification. The etherification reaction is desirably carried out in the presence of a base, e.g. potassium t-butoxide or sodium hydride, and is preferably conducted in an organic solvent, for example dimethylsulphoxide, a cyclic ether such as tetrahydrofuran or dioxan, or an N,N-disubstituted amide such as dimethylformamide. Under these conditions the configuration of the oximino group is substantially unchanged by the etherification reaction. This process is particularly useful in the preparation of acid (IV) in which both $R^a$ and $R^b$ are hydrogen.

Acids (IV) may also be prepared by reacting an acid of formula (VI) as defined above with a compound of formula

  (VIII)

(where $R^a$, $R^b$, T, m and n are as hereinbefore defined and $R^{20}$ is a carboxyl blocking group, e.g. a lower alkyl group such as methyl or ethyl) for example using conditions similar to those described above for the reaction of compounds (VI) and (VII), and reacting the resulting compound of formula

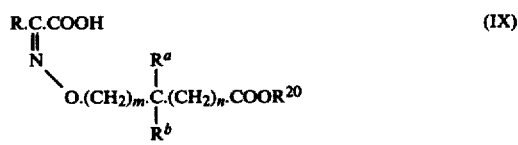  (IX)

with a compound $R^cR^d.NH$ (where $R^c$ is as hereinbefore defined and $R^d$ is lower alkoxy, aralkoxy or aryloxy) to yield an acid of formula (IV). It will be appreciated that when either $R^a$ or $R^b$ is a blocked carboxy (e.g. lower alkoxycarbonyl) group, this group may also be converted to an aminocarbonyl or N-substituted aminocarbonyl group under the reaction conditions. Separation of isomers may be effected at any appropriate stage in the reaction sequence.

Further methods of preparing acids of general formula (IV) are as follows:

(a) Reaction of a glyoxylic acid of formula

  R.CO.COOH  (X)

(wherein R is as defined above) with a compound of formula

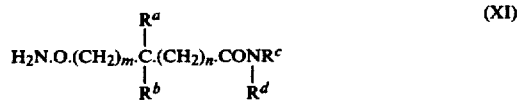  (XI)

(wherein $R^a$, $R^b$, $R^c$, m and n are defined above and $R^d$ is lower alkoxy, aralkoxy or aryloxy); and (b) Reaction of a glyoxylic acid of formula (X) with a compound of formula

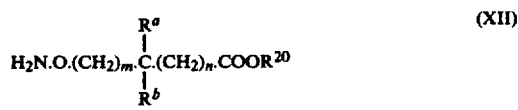  (XII)

(wherein $R^a$, $R^b$, $R^{20}$, m and n are as hereinabove defined) and reaction of the resulting compound of formula (IX) with a compound $R^cR^dNH$. Reaction of (X)

with (XI) or (XII) may be followed where necessary by the separation of syn and anti isomers.

The acids of formula (IV) may be converted to the corresponding acid halides and anhydrides by conventional methods.

Carboxyl blocking groups $R^{19}$ used in the preparation of compounds of formula I or in the preparation of necessary starting materials are desirably groups which may readily be split off at a suitable stage in the reaction sequence, conveniently as the last stage. It may, however, be convenient in some instances to employ biologically acceptable, metabolically labile carboxyl blocking groups such as acyloxymethyl groups (e.g. acetoxymethyl, acetoxyethyl and pivaloyloxymethyl) and retain these in the final product to give a biologically acceptable ester derivative of a compound of formula I.

Suitable carboxyl blocking groups are well known in the art, a list of representative blocked carboxyl groups being included in British Pat. No. 1,399,086. Preferred blocked carboxyl groups include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. The carboxyl blocking group may subsequently be removed by any of the appropriate methods disclosed in the literature. For example, acid-, base- or enzymically-catalysed hydrolysis and reductive methods are applicable in many cases.

The antibiotic compounds of the invention, e.g. compounds of formula I and non-toxic derivatives thereof, may be formulated for administration in any convenient way, by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

The antibiotic compounds may also be presented in a form suitable for absorption by the gastro-intestinal tract, e.g. as tablets or capsules. The antibiotic compounds may also be formulated as suppositories, e.g. containing conventional suppository bases such as cocoa butter or other glyceride.

Compositions for veterinary medicine may, for example, be formulated as intramammary preparations in either long acting or quick-release bases.

The compositions may contain from 0.1% upwards, e.g. 0.1-99%, preferably from 10-60% of the active material, depending on the method of administration. When the compositions comprise dosage units, each unit will preferably contain 50-1500 mg of the active ingredient. The dosage as employed for adult human treatment will preferably range from 500 to 5000 mg per day, depending on the route and frequency of administration, although in treating some infections higher daily doses may be required.

The antibiotic compounds according to the invention may be administered in combination with other therapeutic agents such as antibiotics, for example penicillins or other cephalosporins.

The following examples illustrate the invention. All temperatures are in °C. The structures of the products were verified by p.m.r. and i.r. spectroscopy.

PREPARATION 1

Methyl Chloroacetohydroxamate

Sodium hydrogen carbonate (5.04 g) was added to a solution of methoxyamine hydrochloride (2.51 g) in water (40 ml). Chloroacetyl chloride (2.40 ml) in tetrahydrofuran (20 ml) was added dropwise to the resulting solution during 35 min with stirring, at 0°-3°. The mixture was then stirred for 2 hr at room temperature, the pH was adjusted to 5 (sodium hydrogen carbonate) and most of the tetrahydrofuran was removed under reduced pressure. The pH was adjusted to 5.5 and the solution was saturated with sodium chloride and extracted with chloroform (5×50 ml). The chloroform solution was dried and evaporated, leaving a yellow oil, which was distilled, giving methyl chloroacetohydroxamate, 2.08 g, b.p. 130°/20 mm $\nu_{max}$ (CHBr$_3$) 3360 (NH), 1690 and 1482 (CONH), 1082 cm$^{-1}$ (OMe), $\tau$(DMSO d$_6$) −1.50 (NH), 5.96 (CH$_2$), 6.30 (OCH$_3$).

PREPARATION 2

Diphenylmethyl Chloroacetohydroxamate

This compound was prepared from diphenylmethoxyamine hydrochloride and chloroacetyl chloride by the method described in Preparation 1; m.p. 115°-117° $\nu_{max}$ (CHBr$_3$) include 3400 (NH), 1692 cm$^{-1}$ (CO-N), $\tau$(DMSO d$_6$) 0.55 (NH), 2.60 (Ph) 4.01 (CHPh$_2$), 6.02 (CH$_2$). Yield 86%.

PREPARATION 3

Methyl N-methylchloroacetohydroxamate

This compound was prepared from O,N-dimethyl hydroxylamine hydrochloride and chloroacetyl chloride in a similar manner to Preparation 1; b.p. 116° (bath) 16 mm, $\nu_{max}$ (CHBr$_3$) include 1665 cm$^{-1}$ (CON—), $\tau$(CDCl$_3$), 5.72 (CH$_2$), 6.21 (OMe), 6.75 (NMe). Yield 58%.

PREPARATION 4

Z-2-(Fur-2-yl)-2-(methoxycarbamoylmethoxyimino)acetic acid

Potassium tert-butoxide (6.73 g) was stirred in dry dimethylsulphoxide (30 ml), then Z-2-(fur-2-yl)-2-hydroxyiminoacetic acid (3.11 g) was added to the suspension, which was cooled in an ice-bath, and the mixture was stirred for 1 hr. Methyl chloroacetohydroxamate (2.35 g) in dimethylsulphoxide (2 ml) was added dropwise. The mixture was stirred for 2 hr at room temperature and the resulting solution was poured into ice and water (125 ml). The pH was adjusted to 1 and the solution was saturated with sodium chloride and extracted with ethyl acetate (50+150+4×200 ml), the pH being kept at 1 by addition of more hydrochloric acid as necessary. The ethyl acetate solution was washed with saturated brine (2×50 ml), then dried (Na$_2$SO$_4$) and evaporated, leaving a pale-brown solid. Washing the solid with dichloromethane left the title-compound, 1.56 g, m.p. 129° (decomp.) $\lambda_{max}$ (EtOH) 272.5 nm ($\epsilon$ 14,700), $\nu_{max}$ (Nujol) 3180 (bonded NH), 1753 (CO$_2$H), 1612 and 1522 cm$^{-1}$ (bonded CONH), τ(DMSO d$_6$) 2.10, 3.15, 3.30 (α-furyl), ca. 4.45 (NH, CO$_2$H), 5.42 (CH$_2$), 6.35 (OCH$_3$).

PREPARATION 5

Z-2-(N-Diphenylmethoxycarbamoylmethoxyimino)-2-(fur-2-yl) acetic acid

This was prepared from diphenylmethyl chloroacetohydroxamate and Z-2-(fur-2-yl)-2-hydroxyiminoacetic acid by the method described in Preparation 4; m.p. 138°–140° (from carbon tetrachloride-dichloromethane), λ$_{max}$ (EtOH) 273.5 nm (ε13,900), ν$_{max}$ (CHBr$_3$) 3350 (NH), ca 3600–2100 (bonded OH), 1750 and 1728 (CO$_2$H), 1690 cm$^{-1}$ (CONH), τ(DMSO d$_6$) include 2.09, 3.20 and 3.30 (α-furyl), 2.4–2.8 (Ph), 4.00 (Ph$_2$CH), 5 49 (CH$_2$). Yield 17%.

PREPARATION 6

Z-2-(Fur-2-yl)-2-(N-methoxy-N-methylcarbamoylmethoxyimino) acetic acid

This compound was prepared as in Preparation 4, from methyl N-methylchloroacetohydroxamate, except that only two molar equivalents of potassium tert-butoxide were used for one molar equivalent of Z-2-(fur-2-yl)-2-hydroxy iminoacetic acid. τ(DMSO d$_6$), ca 1.2 (CO$_2$H), 2.11, 3.18, 3.32 (α-furyl), 5.02 (CH$_2$); 6.29 (OMe); 6.86 (NMe). Yield 92%

PREPARATION 7

Z-2(2-N-Diphenylmethoxycarbomoyl-prop-2-yloxyimino)-2-(fur-2-yl)acetic acid

(a) Methyl Z-2-(2-tert-butoxycarbonylprop-2-yloxyimino)-2-(fur-2-yl)acetate Z-2-(2-tert-Butoxycarbonylprop-2-yloxyimino)-2-(fur-2-yl)acetic acid (4.5 g), in ether (7 ml) was methylated with an ethereal solution of diazomethane. The resulting solution was washed with saturated sodium bicarbonate solution (2×20 ml), dried over sodium sulphate and evaporated giving the title ester, 4.67 g, λ$_{max}$, (MeOH) 280 nm (ε16,700), ν$_{max}$ (CHBr$_3$), 1740, 1730 cm$^{-1}$ (—CO$_2$R), τ(DMSO d$_6$) 2.09, 3.16, 3.32 (fur-2-yl), 6.08 (—CO$_2$CH$_3$), 8.54 (—C (Me)$_2$), 8.59 (—CO$_2$tBu).

(b) Methyl-Z-2-(2-carboxyprop-2-yloxyimino)-2-(fur-2-yl) acetate

Methyl-Z-2-(2-tert-butoxycarbonylprop-2-yloxyimino)-2-(fur-2-yl) acetate (4.5 g) was stirred with anisole (15 ml) and trifluoroacetic acid (30 ml) for 30 min. The solution was evaporated and the residue dissolved in ethyl acetate (100 ml) and extracted with saturated sodium bicarbonate solution (4×30 ml). The combined extracts were acidified with 2 N-hydrochloric acid and extracted with ethyl acetate (3×50 ml). The organic layer was dried over sodium sulphate and evaporated giving the title acid, 3.3 g, λ$_{max}$ (MeOH) 280 nm, (ε15,900), ν$_{max}$ (Nujol) 3600–2100 (bonded OH), 1750, 1710 cm$^{-1}$ (CO$_2$R, CO$_2$H), τ(DMSO d$_6$) 2.1, 3.12, 3.3 (fur-2-yl), 6.1 (—CO$_2$Me), 8.52 (C(Me)$_2$).

(c) Methyl Z-2-(2-N-diphenylmethoxycarbamoylprop-2-yloxyimino)-2-(fur-2-yl)acetate Oxalyl chloride (4.03 ml) was added dropwise to a solution of methyl Z-2-(2-carboxyprop-2-yloxyimino)-2-(fur-2-yl) acetate (10.9 g) and triethylamine (5.94 ml) in dichloromethane (60 ml) while stirring at 3° C., and the mixture stirred for 2 hr more at 3° C. The mixture was filtered and the filtrate evaporated and azeotroped with a little benzene. The residue was dissolved in dichloromethane (50 ml) and added dropwise to a mixture of diphenylmethoxyamine (8.5 g) and triethylamine (5.94 ml) in dichloromethane (25 ml) while stirring at 0° C. After the addition was complete the mixture was stirred for 2 hr at 20° C. The mixture was washed with water (2×50 ml), saturated sodium bicarbonate solution (3×15 ml), 2 N-hydrochloric acid (3×15 ml), and brine (20 ml). The organic layer was dried over sodium sulphate and evaporated. The residue was recrystallized from toluene, the solid was filtered off and the filtrate was evaporated giving the required ester 3.97 g. λ$_{max}$ (EtOH), 284.5 nm (ε14,300), ν$_{max}$ (Nujol) 3420 (NH), (CO$_2$R), 1690 cm$^{-1}$ (—CONH—), τ(DMSO d$_6$) 2.1, 3.16, 3.32 (fur-2-yl), 2.5–2.7 (Ph$_2$C), 4.01 (Ph$_2$CH), 6.18 (CO$_2$Me), 8.65 (C(Me)$_2$), −0.6 (NH).

(d) Z-2-(2-N-Diphenylmethoxycarbamoylprop-2-yloxyimino)-2-(fur-2-yl)acetic acid Aqueous sodium hydroxide (N; 17.8 ml) was added dropwise to a solution of methyl-Z-2-(2-N-diphenylmethoxycarbamoylprop-2-yloxyimino)-2-(fur-2-yl)acetate (3.9 g) in methanol (75 ml) while stirring at 0° C. The solution was stirred for 18 hr and adjusted to pH 6 and the methanol evaporated. The aqueous solution was adjusted to pH 8.5, washed with ethyl acetate (20 ml) and acidified with 2 N-hydrochloric acid and extracted with ethyl acetate (3×20 ml). The organic extracts were dried over sodium sulphate and evaporated giving the required acid, 3.2 g, λ$_{max}$ (EtOH) 271.5 nm (ε14,750), ν$_{max}$ (Nujol) 3250 (NH), 3400–2100 (bonded OH), 1712 (—CO$_2$H), 1630 cm$^{-1}$ (—CONH—), DMSO d$_6$) 2.4–2.9 (Ph$_2$C), 4.0 (Ph$_2$CH), −0.6 (—CONHO), 8.67 (C(Me)$_2$), 2.1, 3.25, 3.35 (fur-2-yl).

PREPARATION 8

Z-2-(Fur-2-yl)-2-(N-methoxycarbamoylprop-2-yloxyimino)acetic acid

(a) Methyl Z-2-(fur-2-yl)-2-(N-methoxycarbamoylprop-2-yloxyimino)acetate

This compound was prepared from methyl Z-2(2-carboxylprop-2-yloxyimino)-2-(fur-2-yl)acetate and methoxyamine by the method described in Preparation 7 (c) above. ν$_{max}$ (CHBr$_3$) 3400, 3350 (sh) (NH), 1736 (CO$_2$R), 1690 cm$^{-1}$ (CONH), τ(CDCl$_3$) 2.08, 3.11, 3.29 (α-furyl); 6.38 (OMe), 8.54 (OMe$_2$). Yield 53%.

(b) Z-2-(Fur-2-yl)-2-(N-methoxycarbamoylprop-2-yl yloxyimino) acetic acid

Hydrolysis of the above methyl ester afforded the title compound, λ$_{max}$ (EtOH) 273.5 nm (ε14,800), ν$_{max}$ (Nujol) ca 3600–2000 (bonded OH), 3380 (NH), 1740 and 1720 (CO$_2$H), 1660 cm$^{-1}$ (CONH), τ(DMSO d$_6$) 2.08, 3.11, 3.29 (α-furyl); 6.38 (OMe), 8.54 (CMe$_2$). Yield 85%.

PREPARATION 9

Z-2-(1-N-Diphenylmethoxycarbamoylcyclopent-1-yloxyimino)-2-(fur-2-yl)acetic acid

(a) Methyl Z-2-(1-tert-Butoxycarbonylcyclopent-1-yloxyimino)-2-(fur-2-yl)acetate This compound was prepared from Z-2-(1-tert-butoxycarbonylcyclopent-1-yloxyimino)-2-(fur-2-yl)acetic acid by the method described in Preparation 7(a) above, $\lambda_{max}$ (EtOH), 280.5 nm ($\epsilon$17,300), $\nu_{max}$ (Nujol) 1740, 1725 (sh) cm$^{-1}$ ($CO_2R$), $\tau$(DMSO d$_6$) 2.10, 3.18, 3.34 ($\alpha$-furyl); 6.11 ($CO_2Me$), 7.6–8.8 (cyclopentyl), 8.60 ($CMe_3$). Yield 96%.

(b) Methyl Z-2-(1-carboxycyclopent-1-yloxyimino)-2-(fur-2-yl)acetate

This compound was prepared from the preceding compound by the method described in Preparation 7(b) $\lambda_{max}$ (EtOH) 282 nm ($\epsilon$15,900), $\nu_{max}$ (Nujol) ca 3600–2100 (bonded OH), 1742, 1718, 1702 cm$^{-1}$ ($CO_2R$, $CO_2H$), $\tau$(DMSO d$_6$) 2.10, 3.17, 3.31 ($\alpha$-furyl); ca −3 ($CO_2H$), 6.10 ($CO_2Me$), 7.5–8.6 (cyclopentyl). Yield 90%.

(c) Methyl-Z-2-(1-N-Diphenylmethoxycarbamoylcyclopent-1-yloxyimino)-2-(fur-2-yl)acetate This compound was prepared from the preceding compound by the method described in Preparation 7 (c) above. $\lambda_{max}$ (EtOH) 286 nm ($\epsilon$14,900), $\nu_{max}$ (Nujol) 3420 (NH), 1750 ($CO_2R$), 1690 cm$^{-1}$ (CONH), $\tau$(DMSO d$_6$) 2.11, 3.20, 3.30 ($\alpha$-furyl); 2.3–2.8 (Ph), 3.95 (CHPh$_2$), 6.10 ($CO_2Me$), 7.4–7.8 (cyclopentyl). Yield 38%.

(d) Z-2-(1-N-Diphenylmethoxycarbamoylcyclopent-1-yloxyimino)-2-(fur-2-yl)acetic acid This compound, prepared from the preceding compound by the method described in Preparation 7 (d) above, was obtained as the sodium salt $\lambda_{max}$ (EtOH) 272.5 nm ($\epsilon$12,200), $\nu_{max}$ (Nujol) 3700–2200 (bonded OH), 3400 (NH), 1655, 1510 (CONH), 1615 cm$^{-1}$ ($CO_2^-$), $\tau$(DMSO d$_6$) −3.1 (CONHO), 2.30, 3.38, 3.49 ($\alpha$-furyl), 2.5–3.0 (Ph), 3.99 (CHPh$_2$), 7.8–8.7 (cyclopentyl). Yield 95%.

PREPARATION 10

(a) Methyl 2-(methoxycarbamoylcyclopent-1-yloxyimino)2-(fur-2-yl)acetate

This compound was prepared from methyl Z-2-(carboxycyclopent-1-yloxyimino)-2-(fur-2-yl)acetate and methoxyamine as described in Preparation 7(c) $\nu_{max}$ (CHBr$_3$) 3400, 3350 (—NH—), 1740 (—$CO_2R$), 1686 cm$^{-1}$ (—CONH—), $\tau$(DMSO d$_6$), 6.4 (—OMe), −0.88 (—CONHO), 7.7–8.7 (cylopentyl), 2.1, 3.1, 3.3 (furyl), 6.1 (—$CO_2Me$). Yield 75%

(b) Z-2-(Fur-2-yl)-2-(methoxycarbamoylcyclopent-1-yloxyimino)acetic acid

This compound was prepared from methyl Z-2-(fur-2-yl)-2-(methoxycarbamoylcyclopent-1-yloxyimino)acetate as described in Preparation 7(d). It was obtained as a pale brown foam, of which part was the sodium salt, $\nu_{max}$ (Nujol) 3220 (—NH—), 3700–1800 (bonded OH), 1740, 1707 (—$CO_2H$), 1625, 1512 cm$^{-1}$ (—CONH—, —$CO_2^{\ominus}$), $\tau$(DMSO d$_6$) 6.4 (—$OCH_3$), 7.7–8.6 (cyclopentyl), 2.18, 3.20, 3.38 (furyl). Yield 87%.

PREPARATION 11

(a) Methyl Z-2-(1-tert-Butyloxycarbonylcyclobutyloxyimino)-2-(fur-2-yl)acetate This compound was prepared from Z-2-(1-tert-butyloxycarbonylcyclobutyloxyimino)-2-(fur-2-yl)acetic acid as described in Preparation 7(a). $\lambda_{max}$ (EtOH) 281.5 nm ($\epsilon$17,000), $\nu_{max}$ (Nujol) 1745 (—$CO_2R$), 1723 cm$^{-1}$ ($\alpha,\beta$-unsaturated —$CO_2R$), $\tau$(DMSO d$_6$) 8.59 (—$C(Me)_3$), 7.3–8.4 (cyclobutane), 2.1, 3.15, 3.35 (furyl), 6.09 (—$CO_2CH_3$). Yield 98%.

(b) Methyl Z-2-(1-Carboxycyclobutyloxyimino)-2-(fur-2-yl)acetate

This compound was prepared from methyl Z-2-(1-tert-butyloxycarbonyloxycyclobutyloxyimino)-2-(fur-2-yl)acetate as described in Preparation 7(b), m.p. 133°–134°. $\lambda_{max}$ (EtOH) 284 nm ($\epsilon$15,900), $\nu_{max}$ (Nujol) 3500–2100 (bonded OH), 1750 ($CO_2H$), 1708 cm$^{-1}$ ($\alpha,\beta$-unsaturated —$CO_2R$), $\tau$(DMSO d$_6$) 7.2–8.5 (cyclobutane), 2.1, 3.12, 3.33 (furyl), 6.09 (—$CO_2CH_3$). Yield 94%

(c) Methyl Z-2-(N-Diphenylmethoxycarbamoylcyclobut-1-yloxyimino)-2-(fur-2-yl)acetate.

This compound was prepared from methyl Z-2-(1-carboxycyclobutyloxyimino)-2-(fur-2-yl)acetate and diphenylmethoxyamine as described in Preparation 7(c) $\lambda_{max}$ (EtOH) 285.5 nm ($\epsilon$12,200) $\nu_{max}$ (CHBr$_3$) 3400 (—NH—), 1738 (—$CO_2R$), 1680 cm$^{-1}$ (—CONH—), $\tau$(DMSO d$_6$) 2.4–2.8 (phenyls), 3.98 (Ph$_2$CH—). −0.6 (—CONHO—), 7.2–9.0 cyclobutane), 2.1, 3.15, 3.30 (furyl), 6.12 (—$CO_2CH_3$). Yield 58%.

(d) Z-2-(N-Diphenylmethoxycarbamoylcyclobut-1-yloxyimino)-2-(fur-2-yl)acetic acid This compound was prepared from methyl Z-2-(N-diphenylmethoxycarbamoylcyclobut-1-yloxyimino)-2-(fur-2-yl)acetate as described in Preparation 7(d). $\lambda_{max}$ (EtOH) 273 nm ($\epsilon$13,400) $\nu_{max}$ (CHBr$_3$) 3600–2200 (bonded OH), 3380, 3260 (—NH—), 1745, 1722 (—$CO_2H$), 1690 cm$^{-1}$ (—CONH—), $\tau$(DMSO d$_6$) 2.1, 3.2, 3.3 (furyl), 7.3–8.8 (cyclobutyl), 3.98 (Ph$_2$CH-), 2.3–2.8 (phenyls). Yield 75%.

PREPARATION 12

E-2-Methoxycarbamoylmethoxyimino-2-(thien-2-yl)acetic acid

This compound was prepared by the method of Preparation 4 from methyl chloroacetohydroxamate and E-2-hydroxyimino-2-(thien-2-yl)acetic acid, $\nu_{max}$ (Nujol) 3380 (—NH—), 1750, 1729 (—$CO_2H$), 3700–2400 (bonded OH), 1690 cm$^{-1}$ (—CONH—), $\tau$(DMSO d$_6$) 2.2–3.0 (thienyl), 5.49 (—$OCH_2CO$—), 6.38 (—$OCH_3$). Yield 34%.

PREPARATION 13

(a) Ethyl chloracetohydroxamate

This compound was prepared from ethoxyamine hydrochloride and chloroacetyl chloride by the method described in Preparation 1, m.p. 56°–59°, $\nu_{max}$ (CHBr$_3$) 3400 (—NH—), 1690 cm$^{-1}$ (—CONH—), $\tau$(DMSO d$_6$) –1.25 (—CON$\underline{H}$O—), 6.0 (ClC$\underline{H}_2$CO—), 6.15 (—OC$\underline{H}_2$—), 8.84 (—CH$_3$). Yield 75%

(b) Z-2-Ethoxycarbamoylmethoxyimino-2-(fur-2-yl)acetic acid

This compound was prepared from ethyl chloroacetohydroxamate and Z-2-(fur-2-yl)-2-hydroxyimino acetic acid by the method described in Preparation 4, $\tau$(DMSO d$_6$) 2.15, 3.2, 3.39 (furyl), 5.48 (—OC$\underline{H}_2$CO—), 6.18 (—OC$\underline{H}_2$—), 8.88 (—CH$_3$). Yield 81%.

PREPARATION 14

(a) Phenyl chloroacetohydroxamate

This compound was prepared from phenoxyamine hydrochloride and chloroacetyl chloride by the method described in Preparation 1, m.p. 126°–128° (decomp.), $\lambda_{max}$ (EtOH) 266.5 nm ($\epsilon$15,400), $\nu_{max}$ (Nujol) 3340, 3260, 3140 (—NH—), 1720, 1710, 1690 cm$^{-1}$ (—CONH—), $\tau$(DMSO d$_6$) 5.79 (ClCH$_2$CO—), –2.2 (—N$\underline{H}$—), 2.3–3.2 (phenyl). Yield 67%

(b) Z-2-(Fur-2-yl)-2-phenoxycarbamoylmethoxyiminoacetic acid

This compound was prepared as described in Preparation 4 from phenyl chloroacetohydroxamate and Z-2-(fur-2-yl)-2-hydroxyiminoacetic acid. $\nu_{max}$ (CHBr$_3$) 3350 (NH), 3700–2100 (bonded OH), 1754, 1725 (—CO$_2$H), 1705, 1680 cm$^{-1}$ (—CONH—), $\tau$(DMSO d$_6$) 2.05, 3.11, 3.29 (furyl), 5.3 (—OCH$_2$CO—), 2.4–3.1 (phenyl). Yield 50%.

PREPARATION 15

(a) Methyl Z-2-(fur-2-yl)-2-(phenoxycarbamoylcyclopent-1-yloxyimino)acetate

This compound prepared from methyl Z-2-(carboxycyclopent-1-yloxyimino)-2-(fur-2-yl)acetate and phenoxyamine hydrochloride as described in Preparation 7(c), was purified by chromatography on silica gel plates in ethyl acetate-light petroleum b.p. 40°–60° (3:1 v/v). $\tau$(DMSO d$_6$) 2.5–3.1 (phenyl), 7.7–8.1, 8.1–8.5 (cyclopentyl), 2.0, 3.28, 3.02 (furyl), 6.03 (methyl). Yield 44%

(b) Z-2-(Fur-2-yl)-2-(phenoxycarbamoylcyclopent-1-yloxyimino)acetic acid

This compound was prepared from the corresponding methyl ester as described in Preparation 7(d). $\lambda_{max}$ (EtOH) 274 nm ($\epsilon$9,800), $\nu_{max}$ (Nujol) 3270 (—NH—), 3400–2200 (bonded OH), 1715 (—CO$_2$H), 1662 cm$^{-1}$ (—CONH—), $\tau$(DMSO d$_6$) 2.3–3.1 (phenyl), 7.7–8.1, 8.1–8.5 (cyclopentyl), 1.81, 2.98, 3.18 (furyl). Yield 77%.

EXAMPLE 1

(a) tert-Butyl (6R,7R)-3-Acetoxymethyl-7-8 Z-2-methoxycarbamoylmethoxyimino)-2-(fur-2-yl) acetamido]-ceph-3-em-4-carboxylate tert-Butyl 7-aminocephalosporanate (491 mg) and Z-2-(fur-2-yl)-2-methoxycarbamoylmethoxyimino)acetic acid (362 mg) were dissolved in ethyl acetate (125 ml). Dicyclohexylcarbodiimide (308 mg) was added and the mixture was stirred for 1.5 hr. The solution was filtered and evaporated to dryness and the residue was redissolved in ethyl acetate (30 ml). The solution was filtered and washed with saturated sodium hydrogen carbonate (25 ml), then with N-hydrochloric acid (2×20 ml), then washed with water (2×10 ml) dried (Na$_2$SO$_4$), and evaporated, leaving the title compound as a yellow froth (839 mg). A sample purified by chromatography on silica in ethyl acetate had $\nu_{max}$ (CHBr$_3$) 3400, 3280 (NH), 1785 ($\beta$-lactam), 1722 (CO$_2$CMe$_3$), ca. 1735 sh; acetate), 1688 and 1512 cm$^{-1}$ (CONH).

(b) (6R,7R)-3-Acetoxymethyl-7-[Z-2-methoxycarbamoylmethoxyimino)-2-(fur-2-yl)acetamido]-ceph-3-em-4-carboxylic acid The corresponding tert-butyl ester (819 mg) was dissolved in trifluoroacetic acid (11 ml) and the solution was left for 10 min at room temperature. The trifluoroacetic acid was removed under reduced pressure and the residual brown foam was dissolved in ethyl acetate (60 ml). The solution was filtered and extracted with saturated sodium hydrogen carbonate solution (2×30 ml). The extract was washed with ethyl acetate (2×30 ml), acidified (2N—HCl) and shaken with ethyl acetate (3×30 ml). The ethyl acetate solution was dried (Na$_2$SO$_4$) and evaporated, leaving the title compound 477 mg $[\alpha]_D^{23}$+32° (c 0.9, DMSO) $\lambda_{max}$ (EtOH) 275 nm ($\epsilon$21,100), $\nu_{max}$ (Nujol) 3700–2200 (bonded OH), 3240 (NH), 1787 ($\beta$-lactam), 1735 (sh; acetate), 1728 (CO$_2$H), 1670 and 1540 cm$^{-1}$ (CONH), $\tau$(DMSO d$_6$) include 0.27 (CONH), 2.10, 3.20 and 3.31 ($\alpha$-furyl), 4.11 (C-7H), 4.79 (C-6H), 5.41 (OCH$_2$CO), 6.37 (OMe), 7.91 (OCOCH$_3$).

EXAMPLES 2–18

(a) The esters listed in Table 1 were prepared by the method described in Example 1 (a). They are identified by reference to the formula:

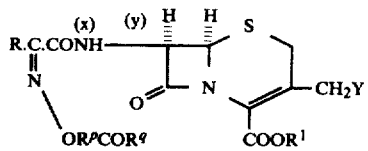

(b) The compounds listed in Table 2 were prepared from the esters given in Table 1 by the following method.

The t-butyl or diphenylmethyl ester was dissolved in a mixture of trifluoroacetic acid and anisole. After about 15 minutes, the trifluoroacetic acid was removed under reduced pressure and the residue was partitioned between sodium hydrogen carbonate and ethyl acetate. The aqueous layer was washed with ethyl acetate and brought to pH 1 (2N—HCl), then extracted several times with ethyl acetate. The extracts were dried (Na$_2$-

SO₄) and evaporated. The residue was filtered off, leaving the title compound.
The compounds are identified in Table 2 by reference to the formula:
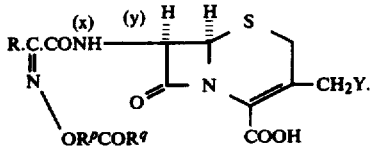

TABLE 1

| Ex. No. | R | $R^p$ | $R^q$ | Y | $R^1$ | pH6 λmax nm | ε | β-lactam $\nu_{max}$ cm$^{-1}$ (solvent) | τ values for DMSO d$_6$ at 100 MHz | | | Yield % |
|---|---|---|---|---|---|---|---|---|---|---|---|---|
| | | | | | | | | | x | OR/COR$^s$ | y | |
| 2a | (furan ring) | —CH$_2$— | H / —N—OCH$_3$ | —OCONH$_2$ | —CHPh$_2$ | | | | 0.22 | 6.40 | 4.04 | 48 |
| 3a | " | —CH$_2$— | H / —N—OCH$_3$ | —OCOCH$_3$ | —C(CH$_3$)$_3$ | | | 1789 | 0.18 | 5.40 | $R^p$ 4.12 | 100 |
| 4a | " | —CH$_2$— | H / —N—OCH$_3$ | —S—(N—N triazole, CH$_3$) | —CHPh$_2$ | | | | 0.18 | 5.40 / 6.30 | $R^p$ / $R^q$ 3.99 | 100 |
| 5a | " | —CH$_2$— | CH$_3$ / —N—OCH$_3$ | —OCOCH$_3$ | —C(CH$_3$)$_3$ | | | | 0.34 | 6.25 / 6.86 | $R^q$ 4.15 | 21 |
| 6a | " | —CH$_2$— | H / —N—OCH$_3$ | —OCONH$_2$ | —CHPh$_2$ | 277. | 15,700 | 1785 | 0.15 | 5.48 | $R^p$ 4.07 | 50 |
| 7a | " | —C(CH$_3$)$_2$ | H / —N—OCH$_3$ | —OCOCH$_3$ | —C(CH$_3$)$_3$ | | | 1788 | 0.32 | 8.4—8.5 | $R^p$ | 63 |
| 8a | " | —C(CH$_3$)$_2$ | H / —N—OCH$_3$ | —OCOCH$_3$ | —C(CH$_3$)$_3$ | | | | 0.30 | 8.50—8.52 / 6.39 | $R^p$ / $R^q$ 4.08 | 100 |
| 9a | " | —C(CH$_3$)$_2$ | H / —N—OCH$_3$ | —OCONH$_2$ | —CHPh$_2$ | | | | 0.29 | 8.51 / 8.38 | $R^p$ / $R^q$ 3.99 | 88 |
| 10a | " | (cyclopentyl) | H / —N—OCHPh$_2$ | —OCONH$_2$ | —CHPh$_2$ | 279.5 | 17,600 | 1788 | 0.35 | 7.6—8.7 | $R^p$ 4.06 | 65 |
| 11a | " | —CH$_2$— | H / —N—OCH$_3$ | —H | —CHPh$_2$ | | | 1780 | 0.22 | 5.4 / 6.32 | $R^p$ / $R^q$ 4.11 | 100 |
| 12a | (furan ring) | —CH$_2$— | H / —N—OCH$_3$ | —S—(N—N thiadiazole, CH$_3$)$_2$CH | —CHPh$_2$ | 277.5 | 24,300 | 1788 | 0.19 | 5.42 / 6.38 | $R^p$ / $R^q$ 4.02 | 44 |

TABLE 1-continued

| Ex. No. | R | R$^p$ | R$^q$ | Y | R$^1$ | pH6 λmax nm | ε | β-lactam ν$_{max}$ cm$^{-1}$ (solvent) | τ values for DMSO d$_6$ at 100 MHz OR/COR$^q$ | | | Yield % |
|---|---|---|---|---|---|---|---|---|---|---|---|---|
| | | | | | | | | | x | | y | |
| 13a | " | (cyclopentyl) | H —N—OCH$_3$ | —OCONH$_2$ | —CHPh$_2$ | | | 1790 | 0.30 | 7.6–8.8 R$^p$<br>6.38 R$^q$ | 3.98 | 97 |
| 14a | " | (cyclobutyl) | H —N—OCHPh$_2$ | —OCONH$_2$ | —CHPh$_2$ | 279.5 | 12,400 | 1788 | 0.21 | 7.2–9.3 R$^p$ | 4.02 | 35 |
| 15a | " | —CH$_2$— (thienyl) | H —N—OCH$_3$ | —OCOCH$_3$ | —C(CH$_3$)$_3$ | | | 1785 | 0.18 | 5.4 R$^p$<br>6.31 R$^q$ | 4.05 | 65 |
| 16a | " | —CH$_2$— (furyl) | H —N—OC$_2$H$_5$ | —OCOCH$_3$ | —C(CH$_3$)$_3$ | | | 1786 | 0.19 | 5.39 R$^p$ | 4.08 | 84 |
| 17a | " | —CH$_2$— (thienyl) | H —N—OPh | —OCOCH$_3$ | —C(CH$_3$)$_3$ | | | | 0.28 | 8.8 R$^q$<br>6.11<br>5.3 R$^p$<br>2.4–3.1 R$^q$<br>−1.7 | 4.08 | 100 |
| 18a | " | (cyclopentyl) | H —N—OPh | —OCOCH$_3$ | —C(CH$_3$)$_3$ | | | | 0.30 | 7.7–8.2 R$^q$<br>8.2–8.8 R$^p$<br>2.4–3.0 | 3.98 | 99 |

TABLE 2

| Ex. | R | $R^p$ | $R^q$ | Y | $[\alpha]_D$ (dioxan) | pH6 $\nu_{max}$ nm | $\varepsilon$ | β-lactam $\nu_{max}$ cm$^{-1}$ (solvent) | τ values for DMSO-d$_6$ at 100 MHz | | | Yield % |
|---|---|---|---|---|---|---|---|---|---|---|---|---|
| | | | | | | | | | x | OR/COR$^q$ | y | |
| 2b | furan-2-yl | —CH$_2$— | H, —N—OCH$_3$ | —OCONH$_2$ | | 273.5 | 18,200 | 1785 | 0.22 | 5.41 ($R^p$) / 6.32 ($R^q$) | 4.15 | 71 |
| 3b | " | —CH$_2$— | H, —N—OH | —OCOCH$_3$ | | 272 | 13,400 | 1782 | 0.11 | −0.4 ($R^q$) | 4.10 | 36 |
| 4b | " | —CH$_2$— | H, —N—OCH$_3$ | —S-(1-methyl-1,2,3,4-tetrazol-5-yl) | | 277.5 | 18,500 | 1782 | 0.18 | −5.40 ($R^p$) / 6.30 ($R^q$) | 4.10 | 73.5 |
| 5b | " | —CH$_2$— | CH$_3$, —N—OCH$_3$ | —OCOCH$_3$ | +29° | 271 | 16,000 | 1788 | 0.23 | 6.26 / 6.82  $R^q$ | 4.12 | 87 |
| 6b | " | —CH$_2$— | H, —N—OH | —OCONH$_2$ | | 276 | 14,200 | 1776 | 0.12 | 5.41 ($R^p$) / 0.36 ($R^q$) | 4.15 | 23 |
| 7b | " | —C(CH$_3$)$_2$ | H, —N—OH | —OCOCH$_3$ | | 272 | 16,000 | 1784 | 0.11 | 8.57 / 8.59  $R^p$ | 4.08 | 32 |
| 8b | " | —C(CH$_3$)$_2$ | H, —N—OCH$_3$ | —OCOCH$_3$ | | 274 | 15,400 | 1788 | 0.38 | −0.1 $R^q$; 8.55 ($R^p$) | 4.05 | 76 |
| 9b | " | —C(CH$_3$)$_2$ | H, —N—OCH$_3$ | —OCONH$_2$ | +50° | 274.5 | 15,800 | 1785 | 0.32 | −0.60 / 6.40 $R^q$; 8.56 ($R^p$); −0.7 $R^q$ | 4.09 | 88 |
| 10b | furan-2-yl | spiro-cyclopentane | H, —N—OH | —OCONH$_2$ | | 274.5 | 14,800 | 1782 | 0.28 | ca 6.4; 7.95, 8.3  $R^p$ | 4.11 | 74 |
| 11b | " | —CH$_2$— | H, —N—OCH$_3$ | —H | | 273.5 | 19,300 | 1780 | 0.26 | −0.08 $R^q$; 5.42 $R^p$ / 6.38 $R^q$ | 4.21 | 64 |

TABLE 2-continued
| Ex. | R | R^p | R^q | Y | [α]_D (dioxan) | pH6 ν_max nm | ε | β-lactam ν_max cm⁻¹ (solvent) | τ values for DMSO-d₆ at 100 MHz x | OR/COR^a | y | Yield % |
|---|---|---|---|---|---|---|---|---|---|---|---|---|
| 12b | " | —CH₂— | H —N—OCH₃ |  | | 278 | 22,200 | 1782 | 0.22 | 5.41 R^p<br>6.39 R^q | 4.12 | 65 |
| 13b | " |  | H —N—OCH₃ | —OCONH₂ | | 274 | 16,400 | 1788 | 0.38 | 7.6–8.7 R^p<br>6.39<br>−0.82 R^q | 4.09 | 28 |
| 14b | " |  | H —N—OH | —OCONH₂ | | 274.5 | 12,400 | 1780 | 0.18 | 7.2–8.6 R^p<br>−0.1 R^q | 4.18 | 47 |
| 15b |  | —CH₂— | H —N—OCH₃ | —OCOCH₃ | +40° | 264 | 12,100 | 1788 | 0.17 | 5.41 R^p<br>6.31 R^q | 4.07 | 66 |
| 16b |  | —CH₂— | H —N—OC₂H₅ | —OCOCH₃ | +33° | 272 | 13,600 | 1782 | 0.2 | 5.4 R^p<br>6.12<br>8.8 R^q | 4.08 | 64 |
| 17b | " | —CH₂— | H —N—OPh | —OCOCH₃ | | 273.5 | 17,300 | 1786 | 0.27 | 5.23 R^p<br>2.4–3.1 R^q | 4.09 | 63 |
| 18b | " |  | H —N—OPh | —OCOCH₃ | | 274. | 15,700 | 1782 | 0.3 | 8.1–8.4 R^p<br>2.3–3.0 R^q | 3.98 | 67 |

EXAMPLE 19

(6R,7R)-7-[Z-2-(fur-2-yl)-2-methoxycarbamoylmethoxyiminoacetamido]-3-(1-pyridiniummethyl)-ceph-3-em-4-carboxylate Sodium iodide (17 g) was dissolved in water (ca 6 ml) at 80° and pyridine (5.5 ml) was added (6R,7R)-3-acetoxymethyl-7-[Z-2-methoxycarbamoylmethoxyimino-2-(fur-2-yl)acetamido]-ceph-3-em-4-carboxylic acid (4.97 g) was added with stirring, during ca 15 min. The mixture was stirred for 55 min. at ca 80° and diluted to 150 ml with water, then shaken with LA2 resin (30 ml) in dichloromethane (70 ml). The aqueous layer was separated and washed with ethyl acetate, then adjusted to pH 1, and extracted with ethyl acetate. The pH was adjusted to 6 and the solution was concentrated to 50 ml and applied to a column of XAD2 resin (500 g). The required compound was eluted with water and the solution was evaporated and freeze-dried, giving a white foam, 1.18 g. A sample was further purified on a similar column, giving the pyridinium compound, $\lambda_{max}$ (EtOH), 282.5 nm ($\epsilon$8,600), $\nu_{max}$ (Nujol) 3220 (—NH—), 1775 ($\beta$-lactam), 1615 (—$CO_2^\theta$), 1670 $cm^{-1}$ (—CONH—), $\tau(D_2O)$ 6.2 (—OMe), 2.22, 3.02, 3.3 (fur-2-yl), 4.03 (7H), 4.69 (6H), 6.3, 6.79 (2—$CH_2$—), 4.38, 4.6 (3—$CH_2$—), 0.98, 1.38, 1.82 (pyridinium).

EXAMPLE 20

Acetoxymethyl (6R,7R)-3-acetoxymethyl-7-[Z-2-methoxycarbamoylmethoxyimino-2-(fur-2-yl)acetamido]-ceph-3-em-4-carboxylate (6R,7R)-3-Acetoxymethyl-7-[Z-2-methoxycarbamoylmethoxyimino-2-(fur-2-yl)acetamido]-ceph-3-em-4-carboxylic acid (992 mg) was dissolved in dry N,N-dimethylformamide (8 ml). Dried potassium carbonate (138 mg) was added and the mixture was stirred at 0°. Iodomethyl acetate (1.1 g) in a little dimethylformamide was added, stirring was continued at 0° for 1 hr, and the mixture was poured into hydrochloric acid (N, 50 ml) and extracted with ethyl acetate (3×50 ml). The ethyl acetate extracts were washed with N-hydrochloric acid (2×50 ml), water (100 ml) and saturated sodium hydrogen carbonate solution (2×30 ml), dried ($Na_2SO_4$) and evaporated. The residue in a little ethyl acetate was added dropwise to well-stirred light petroleum (b.p. 40°-60°), when the ester separated as an off-white powder, 513 mg, $\lambda_{max}$ (EtOH) 277.5 nm, $\nu_{max}$ (Nujol) 3240 (—NH), 1786 ($\beta$-lactam), 1765, 1742 (acetate+—$CO_2CH_2OCOCH_3$), 1680, 1540 $cm^{-1}$ (—CONH—), $\tau(DMSOd_6)$ 6.25 (—$OCH_3$, 2—$CH_2$—), 5.38 (—O—$\underline{CH}_2$—CO—), 2.01, 3.11, 3.22 (fur-2-yl), 0.18 (—CONH—), 4.05 (7H), 4.69 (6H), 4.99, 5.25 (3—$CH_2$—), 7.86, 7.96 (—$COCH_3$), 4.09 (—$O\underline{CH}_2O$—).

Pharmaceutical compositions according to the invention may be formulated according to the following Examples.

EXAMPLE A

(a) Dry Powder for Injection

The sterile sodium salt of (6R,7R)-3-carbamoyloxymethyl-7-[Z-2-(fur-2-yl)-2-(N-hydroxycarbamoylcyclobut-1-yloxyimino)acetamido]ceph-3-em-4-carboxylic acid is filled into glass vials, the claimed contents of each container being 500 mg and 1.0 g of the cephalosporin. Filling is carried out aseptically under a blanket of nitrogen. The vials are closed using rubber discs or plugs held in position by aluminium sealing rings, thereby preventing gaseous exchange or ingress of microorganisms. It would be possible to reconstitute the product by dissolving in water for injections or other suitable sterile vehicle shortly before administration.

(b) Intramammary Injection (for a lactating cow) Percentage Composition (w/w)

| | |
|---|---|
| Sodium salt of the cephalosporin used in (a) | 8.33 |
| Vehicle to: | 100.00 |
| Vehicle: Tween 60 | 3.00 |
| White Beeswax | 6.00 |
| Arachis Oil | 91.00 |

The three ingredients of the vehicle are heated together at 150° C. for one hour and then cooled to room temperature with stirring. The sterile antibiotic, finely powdered, is added aseptically to this vehicle and the product refined with a high speed mixer. The preparation is filled aseptically into sterile containers such as collapsible aluminium tubes or plastic syringes. The fill weight is 3.0 g, each container holding 250 mg of the cephalosporin acid as sodium salt. The product would be intended for administration into the mammary gland through the teat canal.

We claim:
1. An antibiotic compound of the formula

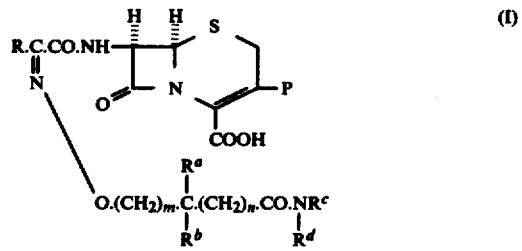

wherein R is phenyl, thienyl or furyl; $R^a$ and $R^b$, which may be the same or different, are each selected from hydrogen, $C_{1-4}$ alkyl, $C_{2-4}$ alkenyl $C_{3-7}$ cycloalkyl, phenyl, naphthyl, thienyl, furyl, carboxy, $C_{2-5}$ alkoxycarbonyl and cyano, or $R^a$ and $R^b$ together with the carbon atom to which they are attached form a $C_{3-7}$ cycloalkylidene or cycloalkenylidene group; $R^c$ is hydrogen or lower alkyl; $R^d$ is hydroxy, lower alkoxy, carbocyclic aryl alkoxy or carbocyclic aryloxy; m and n are each 0 or 1 such that the sum of m and n is 0 or 1; and P is selected from a hydrogen atom, a halogen atom or (a) a group of formula

—XQ wherein X represents oxygen or sulphur and Q represents $C_{1-4}$ alkyl, $C_{2-4}$ alkenyl or aryl $C_{1-4}$ alkyl, (b) a group of formula

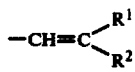

wherein $R_1$ and $R_2$, which may be the same or different, are each selected from hydrogen, carboxy, cyano, $C_{2-7}$ alkoxycarbonyl and $C_{1-6}$ alkyl, and (c) a group of formula

—CH₂Y wherein Y is selected from:
(c) (i) hydrogen,
(c) (ii) the residue of a nitrogen nucleophile which is a tri($C_{1-6}$ alkyl) amine or a heterocyclic tertiary amine,
(c) (iii) azido,
(c) (iv) amino,
(c) (v) alkanoylamino,
(c) (vi) a group of formula

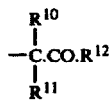

wherein $R^{10}$ and $R^{11}$, which may be the same or different, are each selected from hydrogen; cyano; lower alkyl; phenyl; phenyl substituted by one or more of halo, lower alkyl, lower alkoxy, nitro, amino or lower alkylamino; carboxy; lower alkoxycarbonyl; mono- or di-(carbocyclic aryl) lower alkoxy carbonyl; lower alkylcarbonyl; aryl lower alkyl; and $C_5$ and $C_6$ cycloalkyl; and $R^{12}$ is selected from hydrogen; lower alkyl; phenyl; substituted phenyl; carbocyclic aryl lower alkyl; lower alkoxy; and lower aralkoxy,
(c) (vii) the residue of a sulphur nucleophile which is a thiourea, dithiocarbamate, thioamide, thiosulphate, thioacid or dithioacid,
(c) (viii) a group of formula —S(O)$_n$R$^{13}$ wherein $R^{13}$ is a lower alkyl, lower cycloalkyl, phenyl lower alkyl, $C_{6-12}$ mono- or bicyclic carbocyclic aryl or heterocyclic group containing at least one 5- or 6-membered ring and having one or more heteroatoms selected from O, N, and S, and n is 0, 1 or 2,
(c) (ix) a group of formula

—OR$^{15}$ wherein $R^{15}$ is hydrogen, lower alkyl, lower alkenyl, lower alkynyl, lower cycloalkyl, lower cycloalkyl lower alkyl, aryl, aryl lower alkyl, heterocyclic containing at least one 5- or 6-membered ring and having one or more heteroatoms selected from O, N and S, heterocyclic lower alkyl wherein said heterocyclic contains at least one 5- or 6-membered ring and having one or more heteroatoms selected from O, N and S, or any of the preceding groups for $R^{15}$ substituted by one or more of lower alkoxy, lower alkylthio, halogen, lower alkyl, nitro, hydroxy, acyloxy, carboxy, lower alkoxycarbonyl, lower alkylcarbonyl, lower alkylsulphonyl, lower alkoxysulphonyl, amino, lower alkylamino and alkanoylamino,
(c) (x) a group of formula

—O.CO.R$^{16}$ wherein $R^{16}$ is selected from $C_{1-7}$ alkyl, which may be interrupted by an oxygen or sulphur atom or by an imino group or substituted by cyano, carboxy, lower alkoxycarbonyl, hydroxy, carboxycarbonyl, halogen or amino; $C_{2-7}$ alkenyl, which may be interrupted by an oxygen or sulphur atom or by an imino group; lower cycloalkyl; carbocyclic or a 5- or 6-membered heterocyclic aromatic ring containing at least one atom selected from O, N and S, which may be substituted by hydroxy, halo, nitro, amino, lower alkyl or lower alkylthio; lower cycloalkyl $C_{1-4}$ alkyl; and carbocyclic or heterocyclic aryl $C_{1-4}$ alkyl, and
(c) (xi) a group of formula

—O.CO.AR$^{17}$ wherein $R^{17}$ is hydrogen or a group as defined above for $R^{16}$ and A is $>O$, $>S$ or $>NH$ or a physiologically acceptable salt, ester, 1-oxide or solvate thereof.

2. A compound as claimed in claim 1 which is a syn isomer essentially free from the anti isomer.

3. A compound as claimed in claim 1 wherein P is a group of formula

—CH₂Y in which Y is the residue of a nitrogen nucleophile comprising a pyridine, pyrimidine, pyridazine, pyrazine, pyrazole, imidazole, triazole, thiazole, purine, benzotriazole or any of these compounds substituted by one or more $C_{1-4}$ lower alkyl, phenyl lower alkyl, lower alkoxymethyl, acyloxymethyl, acyl, acyloxy, carboxy, esterified carboxy, carboxy lower alkyl, sulpho, lower alkoxy, phenyl lower alkoxy, lower alkylthio, cyano, hydroxy, carbamoyl, N-mono(lower alkyl)carbamoyl, N,N-di(lower alkyl) carbamoyl, N-(hydroxy lower alkyl) carbamoyl or carbamoyl lower alkyl groups.

4. A compound as claimed in claim 1 wherein P is a group of formula

—CH₂Y in which Y is a group

—SR$^{14}$ wherein $R^{14}$ is a diazolyl, triazolyl, tetrazolyl, thiazolyl, thiadiazolyl, thiatriazolyl oxazolyl, oxadiazolyl, pyridyl, pyrimidyl, benzimidazolyl, benzoxazolyl, benzothiazolyl, triazolopyridyl or purinyl group.

5. A compound as claimed in claim 1 wherein P is an acetoxymethyl or carbamoyloxymethyl group.

6. A compound as claimed in claim 1 having the formula

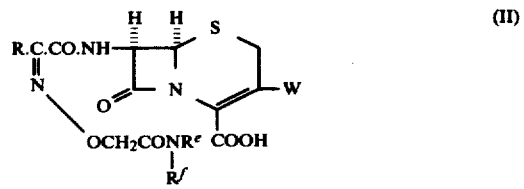

(II)

wherein R is as defined in claim 1; $R^e$ represents a hydrogen atom or a methyl group; $R^f$ represents a hydroxy, methoxy, ethoxy, phenoxy, diphenylmethoxy or triphenylmethoxy; and W is selected from:
(i) acetoxymethyl,
(ii) carbamoyloxymethyl,
(iii) N-methylcarbamoyloxymethyl, (iv) a group of formula

—CH₂G wherein G is the residue of a nitrogen nucleophile selected from compounds of the formula

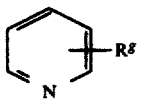

(wherein R^g is hydrogen, carbamoyl, carboxymethyl or sulpho) and pyridazine,
(v) a group of formula —CH₂SR^w wherein R^w is a pyridyl, diazolyl, triazolyl, tetrazolyl, thiazolyl, thiadiazolyl or oxadiazolyl group or a physiologically acceptable salt, ester, 1-oxide or solvate thereof.

7. A compound as claimed in claim 1 having the formula

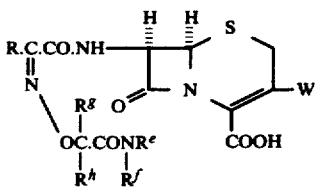

(IIa)

wherein R is as defined in claim 1; R^e represents a hydrogen atom or a methyl group; R^f represents a hydroxy, methoxy, ethoxy, phenoxy, diphenylmethoxy or triphenylmethoxy; and W is selected from:

(i) acetoxymethyl,
(ii) carbamoyloxymethyl,
(iii) N-methylcarbamoyloxymethyl,
(iv) a group of formula

—CH₂G wherein G is the residue of a nitrogen nucleophile selected from compounds of the formula

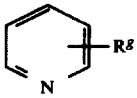

(wherein R^g is hydrogen, carbamoyl, carboxymethyl or sulpho) and pyridazine,
(v) a group of formula —CH₂SR^w wherein R^w is a pyridyl, diazolyl, triazolyl, tetrazolyl, thiazolyl, thiadiazolyl or oxadiazolyl group, and R^g' represents methyl, ethyl, propyl, allyl or phenyl and R^h represents hydrogen, carboxy or a group as defined for R^g'; or R^g' and R^h together with the carbon atom to which they are attached form a cyclobutylidene, cyclopentylidene or cyclohexylidene group or a physiologically acceptable salt, ester, 1-oxide or solvate thereof.

8. A compound as claimed in claim 7 wherein W is a group of formula

—CH₂SR^w in which R^w is 1-methyltetrazol-5-yl or 5-methyl-1,3,4-thiadiazol-2-yl.

9. A compound as claimed in claim 1, said compound being (6R,7R)-3-acetoxymethyl-7-[2-methoxycarbamoylmethoxyimino)-2-(fur-2-yl)acetamido]ceph-3-em-4-carboxylic acid (syn isomer).

10. A compound as claimed in claim 1, said compound being (6R,7R)-3-carbamoyloxymethyl-7-[2-methoxycarbamoylmethoxyimino)-2-(fur-2-yl)acetamido]ceph-3-em-4-carboxylic acid (syn isomer).

11. A compound as claimed in claim 1, said compound being (6R,7R)-3-acetoxymethyl-7-[2-(fur-2-yl)-2-(N-diphenylmethoxycarbamoylmethoxyimino)acetamido]ceph-3-em-4-carboxylic acid (syn isomer).

12. A compound as claimed in claim 1, said compound being (6R,7R)-7-[2-(fur-2-yl)-2-(N-methoxycarbamoylmethoxyiminoacetamido)]-3-(1-methyltetrazol-5-ylthiomethyl)-ceph-3-em-4-carboxylic acid (syn isomer).

13. A compound as claimed in claim 1, said compound being (6R,7R)-3-acetoxymethyl-7-[2-(fur-2-(N-methoxy-N-methylcarbamoylmethoxyimino)acetamido]ceph-3-em-4-carboxylic acid (syn isomer).

14. A compound as claimed in claim 1, said compound being (6R,7R)-3-carbamoyloxymethyl-7-[2-N-diphenylmethoxycarbamoylmethoxyimino)-2-(fur-2-yl)acetamido]ceph-3-em-4-carboxylic acid (syn isomer).

15. A compound as claimed in claim 1, said compound being (6R,7R)-3-acetoxymethyl-7-[2-(2-N-diphenylmethoxycarbamoylprop-2-yloxyimino)-2-(fur-2-yl)acetamido]ceph-3-em-4-carboxylic acid (syn isomer).

16. A compound as claimed in claim 1, said compound being (6R,7R)-3-acetoxymethyl-7-[2-(fur-2-yl)-2-(N-methoxycarbamoylprop-2-yloxyimino)acetamido]-ceph-3-em-4-carboxylic acid (syn isomer).

17. A compound as claimed in claim 1, said compound being (6R,7R)-3-carbamoyloxymethyl-7-[2-(fur-2-yl)-2(N-methoxycarbamoylprop-2-yloxyimino)acetamido]-ceph-3-em-4-carboxylic acid (syn isomer).

18. The compound (6R,7R)-3-acetoxymethyl-7-[2-(fur-2-yl)-2-(N-hydroxycarbamoylmethoxyimino)acetamido]-ceph-3-em-4-carboxylic acid (syn isomer) or a physiologically acceptable salt, ester, 1-oxide or solvate thereof.

19. A compound as claimed in claim 1, said compound being (6R,7R)-3-carbamoyloxymethyl-7-[2-(fur-2-yl)-2-(N-hydroxycarbamoylmethoxyimino)acetamido]ceph-3-em-4-carboxylic acid (syn isomer).

20. A compound as claimed in claim 1, said compound being (6R,7R)-3-acetoxy-methyl-7-[2-(fur-2-yl)-2-(N-hydroxycarbamoylprop-2-yloxyimino)acetamido]ceph-3-em-4-carboxylic acid (syn isomer).

21. A compound as claimed in claim 1 said compound being (6R,7R)-3-carbamoyloxymethyl-7-[2-(fur-2-yl)-2-(N-hydroxycarbamoylcyclopent-1-yloxyimino)acetamido]-ceph-3-em-4-carboxylic acid (syn isomer).

* * * * *